United States Patent [19]

Katsunuma et al.

[11] Patent Number: 4,904,771
[45] Date of Patent: Feb. 27, 1990

[54] PSEUDOURIDINE DERIVATIVE

[76] Inventors: Nobuhiko Katsunuma, 246-2, Myodo 3-chome; Hiroshi Kido, 11-10, Higashiyoshinomachi 3-chome, both of Tokushima-shi, Tokushima-ken; Ikutoshi Matsuura, 1043-67, Ohazashimotomi, Tokorozawa-shi, Saitama-ken; Yoshihiko Ishitani, 8-6, Nakanodaikashimacho, Noda-shi, Chiba-ken, all of Japan

[21] Appl. No.: 142,856

[22] PCT Filed: Apr. 3, 1987

[86] PCT No.: PCT/JP87/00209
§ 371 Date: Dec. 3, 1987
§ 102(e) Date: Dec. 3, 1987

[87] PCT Pub. No.: WO87/05901
PCT Pub. Date: Oct. 8, 1987

[30] Foreign Application Priority Data

Apr. 4, 1986 [JP] Japan .................................. 61-78045

[51] Int. Cl.⁴ .......................... C07G 37/00; C07H 5/04; C07H 15/00; A01N 43/04
[52] U.S. Cl. ..................................... 536/55; 536/18.7; 536/17.4; 536/17.2
[58] Field of Search ....................... 536/55, 18.7, 17.4, 536/17.2

[56] References Cited

U.S. PATENT DOCUMENTS 3,935,184 1/1976 Jones et al. ............................. 536/55
3,988,314 10/1976 Argoudelis et al. ................... 536/55
4,849,513 7/1989 Smith et al. ............................ 536/27

OTHER PUBLICATIONS

Journal of Heterocyclic Chemistry, vol. 12, No. 4, pp. 817 to 818 (1975).

Primary Examiner—Ronald W. Griffin
Assistant Examiner—Everett White
Attorney, Agent, or Firm—Browdy and Neimark

[57] ABSTRACT

5'-Pseudouridyl-N-oleoyl carbamate represented by the formula:

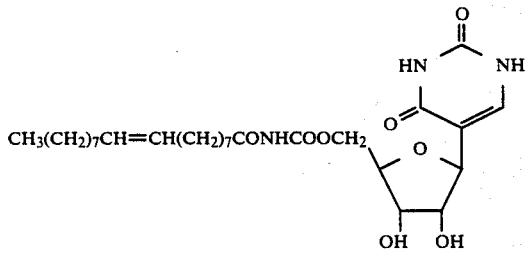

This compound is physiologically active in that it markedly enhances the actions of glucocorticoids and hence is useful as an alternative to conventional steroid drugs.

2 Claims, No Drawings

PSEUDOURIDINE DERIVATIVE

TECHNICAL FIELD

The present invention relates to a novel pseudouridine derivative that enhances the actions of glucocorticoids. The compound of the present invention is physiologically active in such a way that when used in a very small amount it appreciably enhances the actions of glucocorticoids in physiological concentrations. This compound has the potential to replace steroid drugs, the use of which may cause untoward side effects.

BACKGROUND ART

Glucocorticoids that are steroid hormones secreted from the adrenal cortex and which take part in carbohydrate metabolism are responsible for such phenomena as gluconeogenesis in the liver, promotion of hepatic glycogen storage, and increases in blood glucose levels. It has been desired to develop drugs that reduce or obviate that need to administer steroid drugs, which have strong side effects, by enhancing these actions of glucocorticoids.

DISCLOSURE OF THE INVENTION

The present inventors previously found that substances capable of enhancing the actions of glucocorticoids exist in certain components of enterobacteria. On the basis of this finding, the present inventors undertook investigative work to search for such substances. In the course of this work, the present inventors found that 5'-pseudouridyl-N-oleoyl carbamate represented by the following formula (I) has a very strong glucocorticoid enhancing activity, and the present invention has been accomplished as a result of further studies based on this finding:

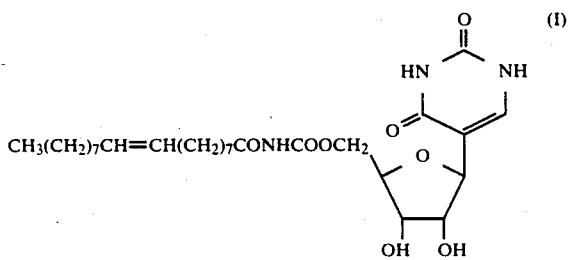

(I)

The compound of the present invention has a unique structure in that naturally occurring oleic acid and pseudouridine are linked with carbamate. There has been no reported case of using a compound with this chemical structure as a physiologically active substance.

The compound of the present invention is novel and may be prepared by reacting pseudouridine with oleoyl isocyanate in an inert solvent.

The glucocorticoid activity enhancing action of the compound of the present invention was verified by screening on rats with induction of tyrosine aminotransferase, which is the principal activity of glucocorticoids, being used as an index (see the Experiment to be noted below).

The following Experiment and Example are provided for the purpose of further illustrating the present invention but are in no way to be taken as limiting its scope.

EXPERIMENT

The physiological activity of 5'-pseudouridyl-N-oleoyl carbamate was verified by measuring its capability to enhance the ability of glucocorticoids to induce tyrosine aminotransferase (EC 2.6.1.5).

Wistar male rats (weighing 190–220 g) were adrenalectomized 7 or 8 days before the experiment. Thereafter, the animals were fed a laboratory diet and aqueous sodium chloride ad libitum. A solution of 5'-pseudouridyl-N-oleoyl carbamate in physiological saline (containing 10% dimethyl sulfoxide) and/or a solution of glucocorticoid in physiological saline was injected intraperitoneally into the adrenalectomized rats. Five hours later, the rats were slaughtered by twisting their necks. The liver was extracted from each rat and homogenized in six volumes of a 0.25M sucrose buffer solution (50 mM potassium phosphate buffer solution containing 1 mM of 2-oxoglutarate and 48 $\mu$M of pyridoxal phosphate; pH, 7.5). The activity of tyrosine aminotranferase in the liver homogenate was measured by the method of Rosen et al. [J. Biol. Chem., 283, 3725–3729 (1963)]. The protein concentration was measured by the method of Lowry et al. [J. Biol. Chem., 173, 265–275 (1951)]. The results are shown in the following table.

The compound of the present invention was found to have the capability to enhance the actions of dexamethasone, hydrocotisone and triamcinolone which are present in limited amounts.

TABLE

| Treatment (nmol/100 g of body weight) | Specific activity of tyrosine aminotransferase (mU/mg of protein) |
|---|---|
| Physiological saline | 7.0 ± 1.1 |
| Compound of the present invention (72) | 7.0 ± 1.2 |
| Dex* (1) | 15.1 ± 1.4 |
| Dex* (1) + compound of the present invention (18) | 22.3 ± 1.8 |
| Dex* (1) + compound of the present invention (36) | 28.6 ± 2.4 |
| Dex* (1) + compound of the present invention (72) | 29.4 ± 2.2 |
| Dex* (1) + compound of the present invention (90) | 29.7 ± 2.6 |
| Hydrocortisone** (600) | 9.5 ± 1.0 |
| Hydrocortisone** (600) + compound of the present invention (72) | 15.0 ± 1.1 |
| Triamcinolone** (1) | 8.8 ± 1.3 |
| Triamcinolone** (1) + compound of the present invention (72) | 18.5 ± 1.6 |

*Dex: Dexamethasone sodium sulfate (Merck & Co.)
**Hydrocortisone and triamcinolone: Both Manufactured by Sigma Chemical Co.

EXAMPLE

Pseudouridine was thoroughly dried on phosphorus pentoxide under vacuum. A portion (530 mg) of the dried pseudouridine was dissolved in 2 ml of dimethyl sulfoxide with heating. To the solution, 1.2 g of oleoyl isocyanate was added under water-cooling and the mixture was stirred for 1 hour. To the reaction product, 200 ml of water was added and the resulting precipitate was recovered by filtration, washed with water and dried with air. The washings were freeze-dried. The air-dried precipitate and freeze-dried precipitate were combined and dissolved in chloroform. The solution was applied to column of silica gel, followed by sequential elution with 500 ml each of 4% methanol-chloroform, 5% methanol-chloroform and 6% methanol-chloroform. The desired 5′-pseudouridyl-N-oleoyl carbamate was obtained in a yield of 190 mg from the fraction of 6% methanol-chloroform. This compound had a melting point of 150°–160° C. (with decomposition).

Elemental analysis: for $C_{28}H_{45}N_3O_8 \cdot \frac{1}{4}H_2O$:

Found (%): C, 60.47; H, 8.25; N, 7.56. Calculated (%): C, 60.49; H, 8.27; N, 7.48.

$^1$H-NMR spectrum δ (ppm) DMSO-d$_6$ (TMS): 11.12(1H,s), 10.86(1H,br.s), 10.52(1H,s) 7.34(1H,br.s), 5.32(2H,t,J=4.6 Hz), 5.03(1H,d,J=4.9 Hz). 4.97(1H,d,J=5.3 Hz), 4.50(1H,d,J=4.4 Hz), 3.80–4.30(5H,m), 2.41(2H,t,J=7.3 Hz), 1.98(4H,br.q,J=5.3 Hz), 1.48(2H,m), 1.24(20H,s), 0.85(3H,t,J=6.3 Hz).

We claim:

1. 5′-Pseudouridyl-N-oleoyl carbamate represented by the formula:

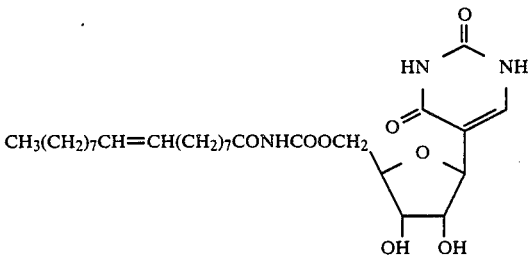

2. A pharmaceutical composition comprising 5′-pseudouridyl-N-oleoyl carbamate and a pharmaceutically acceptable carrier.

* * * * *